(12) United States Patent
Sasaki et al.

(10) Patent No.: US 12,419,674 B2
(45) Date of Patent: *Sep. 23, 2025

(54) MANUAL MIXER

(71) Applicant: Medtronic Europe Sàrl, Tolochenaz (CH)

(72) Inventors: Neil Sasaki, San Jose, CA (US); Mollie Benson, Austin, TX (US); Sarah Freesemann, Bakersfield, CA (US); Benjamin Murray, Union City, CA (US); Aj Konnath, Colorado Springs, CO (US)

(73) Assignee: Medtronic Europe Sàrl, Tolochenaz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/439,179

(22) Filed: Feb. 12, 2024

(65) Prior Publication Data

US 2024/0180602 A1 Jun. 6, 2024

Related U.S. Application Data

(62) Division of application No. 17/097,756, filed on Nov. 13, 2020, now Pat. No. 11,896,276, which is a
(Continued)

(51) Int. Cl.
*A61B 17/00* (2006.01)
*A61B 17/88* (2006.01)
(Continued)

(52) U.S. Cl.
CPC ........ *A61B 17/8833* (2013.01); *B01F 27/112* (2022.01); *B01F 27/13* (2022.01);
(Continued)

(58) Field of Classification Search
CPC ................. A61B 17/8833; A61B 2017/8838
See application file for complete search history.

(56) References Cited

U.S. PATENT DOCUMENTS

| 6,367,962 B1 | 4/2002 | Mizutani |
| 6,712,794 B2 | 3/2004 | Kust |
(Continued)

FOREIGN PATENT DOCUMENTS

| CN | 105147384 | 6/2017 |
| EP | 868209 | 10/1998 |
| EP | 3524342 | 8/2019 |

OTHER PUBLICATIONS

European Search Report issued Jul. 11, 2019 in European Application No. 18212189.7.
(Continued)

*Primary Examiner* — Anshu Bhatia
(74) *Attorney, Agent, or Firm* — Fortem IP LLP

(57) ABSTRACT

A manual mixer serves to facilitate mixing and agitating materials for use during surgery. The manual mixer includes a mixing assembly and an actuation assembly for actuating the mixing assembly. The mixing assembly includes at least a paddle portion and a plunger portion. The plunger portion is simultaneously capable of rotational movement with the paddle portion and movement upwardly or downwardly along the paddle portion. Rotation of the paddle portion serves to facilitate mixing and agitating of the materials, and downward movement of the plunger portion serves to facilitate dispensing of the materials from the manual mixer.

20 Claims, 7 Drawing Sheets

Related U.S. Application Data division of application No. 15/876,256, filed on Jan. 22, 2018, now Pat. No. 10,856,923.

(51) Int. Cl.
| | |
|---|---|
| *B01F 27/112* | (2022.01) |
| *B01F 27/13* | (2022.01) |
| *B01F 27/96* | (2022.01) |
| *B01F 33/501* | (2022.01) |
| *B01F 35/32* | (2022.01) |
| *B01F 35/71* | (2022.01) |
| *B01F 35/75* | (2022.01) |
| B01F 35/33 | (2022.01) |
| B01F 101/20 | (2022.01) |

(52) U.S. Cl.
CPC ........ *B01F 27/96* (2022.01); *B01F 33/50112* (2022.01); *B01F 33/5012* (2022.01); *B01F 35/3202* (2022.01); *B01F 35/7174* (2022.01); *B01F 35/752* (2022.01); *B01F 35/754251* (2022.01); *A61B 2017/8838* (2013.01); *B01F 35/33* (2022.01); *B01F 2101/20* (2022.01)

(56) References Cited

U.S. PATENT DOCUMENTS

| | | | |
|---|---|---|---|
| 6,755,563 | B2 | 6/2004 | Wahlig et al. |
| 7,524,103 | B2 | 4/2009 | McGill et al. |
| 9,694,514 | B2 | 7/2017 | Vogt |
| 10,856,923 | B2 * | 12/2020 | Sasaki .................. B01F 35/752 |
| 2006/0250888 | A1 | 11/2006 | Foster |
| 2009/0281549 | A1 * | 11/2009 | Dixon ................ A61B 17/8833 |
| | | | 366/50 |
| 2013/0310840 | A1 | 11/2013 | Dixon |
| 2015/0103616 | A1 | 4/2015 | Giffard |
| 2015/0164568 | A1 | 6/2015 | Vogt |
| 2016/0278836 | A1 | 9/2016 | Foster et al. |
| 2017/0087527 | A1 | 3/2017 | Vogt |
| 2017/0095283 | A1 | 4/2017 | Vogt |
| 2017/0216790 | A1 | 8/2017 | Sasaki |
| 2017/0291153 | A1 | 10/2017 | Vogt |

OTHER PUBLICATIONS

Australian Examination Report issued Sep. 27, 2023 in Australian Application No. AU2018274974.
Korean Office Action issued Dec. 19, 2023 Korean Application No. 10-2019-0006938 with Translation.
Korean Office Action issued Apr. 5, 2024 Korean Application No. 10-2019-0006938 with Translation.

* cited by examiner

MANUAL MIXER

The present application is a divisional of U.S. application Ser. No. 17/097,756, filed Nov. 13, 2020; which is a divisional of U.S. application Ser. No. 15/876,256, filed Jan. 22, 2018, all of which are incorporated by reference herein.

BACKGROUND OF THE INVENTION

Field of the Invention

The present invention relates to a manual mixer for use during surgery. More particularly, the present invention relates to a manual mixer for mixing and agitating materials including liquids, pastes, and solids added thereto. More specifically, the present invention relates to a manual mixer for mixing and agitating materials through rotational and axial movement of portions of a mixing assembly actuated by an actuation assembly, and for dispensing the materials through a valve assembly.

Description of the Prior Art

Typically, materials such as liquids, pastes, and/or solids used during surgery must be prepared prior to their use. For example, many bone cements require mixing and agitation to prepare the cements for use in patients. Oftentimes, the active ingredients need to be activated via mixing/agitation of the materials during surgery. Otherwise, the bone cement, for example, could harden before it is needed during surgery. Therefore, there is a need for a mixer that allows for easy mixing and agitation of materials during surgery so that the active ingredients can be activated. Such a mixer should be easy to manually operate, provide easy access to a mixing chamber thereof so that the ingredients for the bone cement can be deposited therein, and provide at least two mechanisms by which the materials can be mixed and agitated. Such a manual mixer should also afford easy dispensing therefrom so that the materials mixed and agitated thereby can be easily accessed for use during surgery.

SUMMARY OF THE INVENTION

The present invention in one preferred embodiment contemplates a manual mixer for mixing and agitating materials for use during surgery, the manual mixer including a base portion having a first sidewall portion and a pedestal portion, the first sidewall portion extending upwardly from the pedestal portion and defining at least in part a first interior cavity; a body portion having a second sidewall portion, the second sidewall portion extending upwardly from adjacent the pedestal portion and defining at least in part a second interior cavity, an interior surface of the second sidewall including first threads, and a portion of first sidewall being received with the second interior cavity; a mixing assembly having a paddle portion and a plunger portion, the paddle portion and the plunger portion being provided in portions of the first interior cavity and the second interior cavity, the paddle portion including an upper first end, an opposite lower second end, a length between the upper first end and the lower second end, a first side, an opposite second side, a first substantially planar surface on the first side, a second substantially planar surface on the second side, and at least one opening extending through the paddle portion between the first substantially planar first surface and the second substantially planar second surface, the plunger portion including an upper first end, an opposite lower second end, a length between the upper first end and the lower second end, a first end surface, an opposite second end surface, a first aperture in the first end surface, a second aperture in the second end surface, a passageway extending between the first aperture and the second aperture, and second threads for engaging the first threads formed on the interior surface positioned adjacent the upper first end, at least a portion of the paddle portion being received in the passageway to moveably attach the plunger portion to the paddle portion, the plunger portion being moveable along the paddle portion between an upper first position and a lower second position; a clamp portion receivable in the second interior cavity for engaging the plunger portion to maintain the plunger portion in the upper first position; and an actuation assembly having a transmission housing, a transmission, and a drive shaft, the transmission housing including a third sidewall portion, the third sidewall portion extending upwardly from adjacent the second sidewall portion and defining a third interior cavity, the transmission and a portion of the drive shaft being received in the third interior cavity, the transmission being operatively engaged to the drive shaft and the paddle portion; where actuation of the actuation assembly causes linear movement of the drive shaft, and the linear movement of the drive shaft is translated into rotational movement by the transmission causing corresponding rotation of the paddle portion and the plunger portion moveably attached to the paddle portion; and where, when the clamp portion is received in the second interior cavity and engaged to the plunger portion, the first threads and the second threads are disengaged from one another, and the plunger portion remains in the upper first position during rotation thereof, and, when the clamp portion is removed from the second interior cavity and disengaged from the plunger portion, the plunger portion moves downwardly to engage the first threads and the second threads, and the plunger portion translates toward the lower second position during rotation thereof due to the interaction of the first threads and the second threads.

The present invention in another preferred embodiment contemplates a manual mixer for mixing and agitating materials for use during surgery, the manual mixer including a base portion having a first sidewall portion and a pedestal portion, the first sidewall portion extending upwardly from the pedestal portion and defining at least in part a first interior cavity; a body portion having a second sidewall portion, the second sidewall portion extending upwardly from adjacent the pedestal portion and defining at least in part a second interior cavity, an interior surface of the second sidewall including first threads, and a portion of first sidewall being received with the second interior cavity; a mixing assembly having a paddle portion and a plunger portion, the paddle portion and the plunger portion being provided in portions of the first interior cavity and the second interior cavity, the paddle portion including an upper first end, an opposite lower second end, a length between the upper first end and the lower second end, a first side, an opposite second side, and at least one opening extending through the paddle portion between the first side and the second side, the plunger portion including an upper first end, an opposite lower second end, a length between the upper first end and the lower second end, a first end surface, an opposite second end surface, a first aperture in the first end surface, a second aperture in the second end surface, a passageway extending between the first aperture and the second aperture, and second threads for engaging the first threads formed on the interior surface positioned adjacent the upper first end, at least a portion of the paddle portion being received in the passageway to moveably attach the plunger portion to the paddle portion, the plunger portion being moveable along the paddle portion between an upper first position and a lower second position; and an actuation assembly having a transmission housing, a transmission, and a drive shaft, the transmission housing including a third sidewall portion, the third sidewall portion extending upwardly from adjacent the second sidewall portion and defining a third interior cavity, the transmission and a portion of the drive shaft being received in the third interior cavity, the transmission being operatively engaged to the drive shaft and the paddle portion; where, when the first threads and the second threads are engaged with one another, actuation of the actuation assembly causes linear movement of the drive shaft, and the linear movement of the drive shaft is translated into rotational movement by the transmission causing corresponding rotation of the paddle portion and the plunger portion moveably attached to the paddle portion, and causing translation of the plunger portion toward the lower second position due to the interaction of the first threads and the second threads.

The present invention in yet another preferred embodiment contemplates a method of mixing and agitating materials using a manual mixer, the method including providing the manual mixer having a body portion, a mixing assembly, and an actuation assembly, the body portion defining an interior cavity for receiving at least a portion of the mixing assembly, the mixing assembly including a paddle portion and a plunger portion, a portion of the paddle portion being received within an aperture extending through the plunger portion, the plunger portion being moveable downwardly along the paddle portion, and the actuation assembly being operatively interconnected with the mixing assembly; removing the mixing assembly from the interior cavity; providing the materials to be mixed and agitated in the interior cavity; replacing the mixing assembly in the interior cavity; and actuating the actuation assembly to rotate the paddle portion and the plunger portion, and simultaneously move the plunger portion downwardly along the paddle portion within the interior cavity, the rotation of the paddle portion and the plunger portion, and downwards movement of the plunger portion serving to mix and agitate the materials provided in the interior cavity.

DETAILED DESCRIPTION OF THE PREFERRED EMBODIMENT

In accordance with one preferred embodiment of the present invention, and as depicted in FIGS. 1, 2, and 4-6, a manual mixer 10 is provided for mixing and agitating materials for use during surgery.

Figure 1:
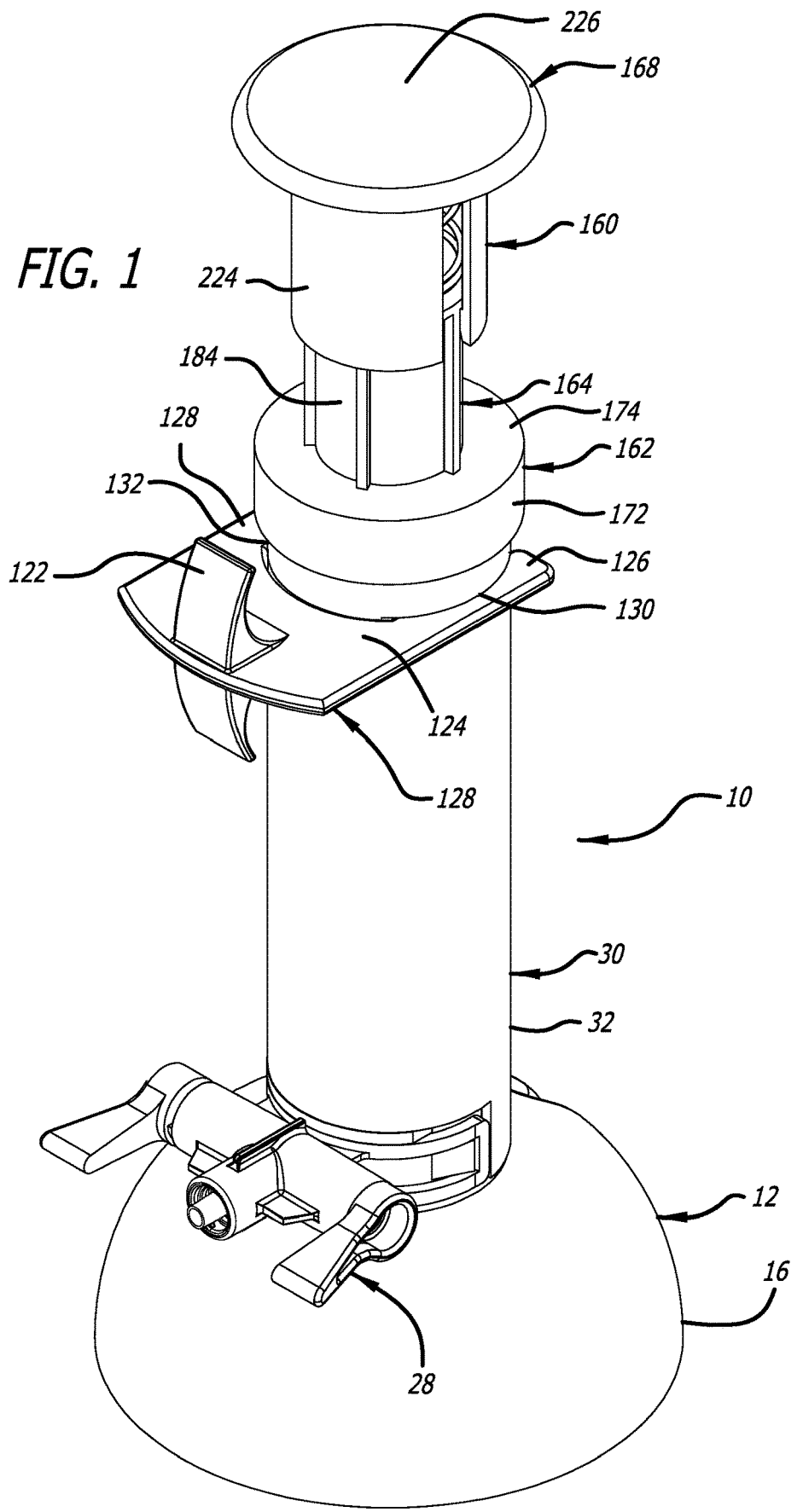
FIG. 1 is a perspective view of a manual mixer according to an embodiment of the present invention.
Figure 2:
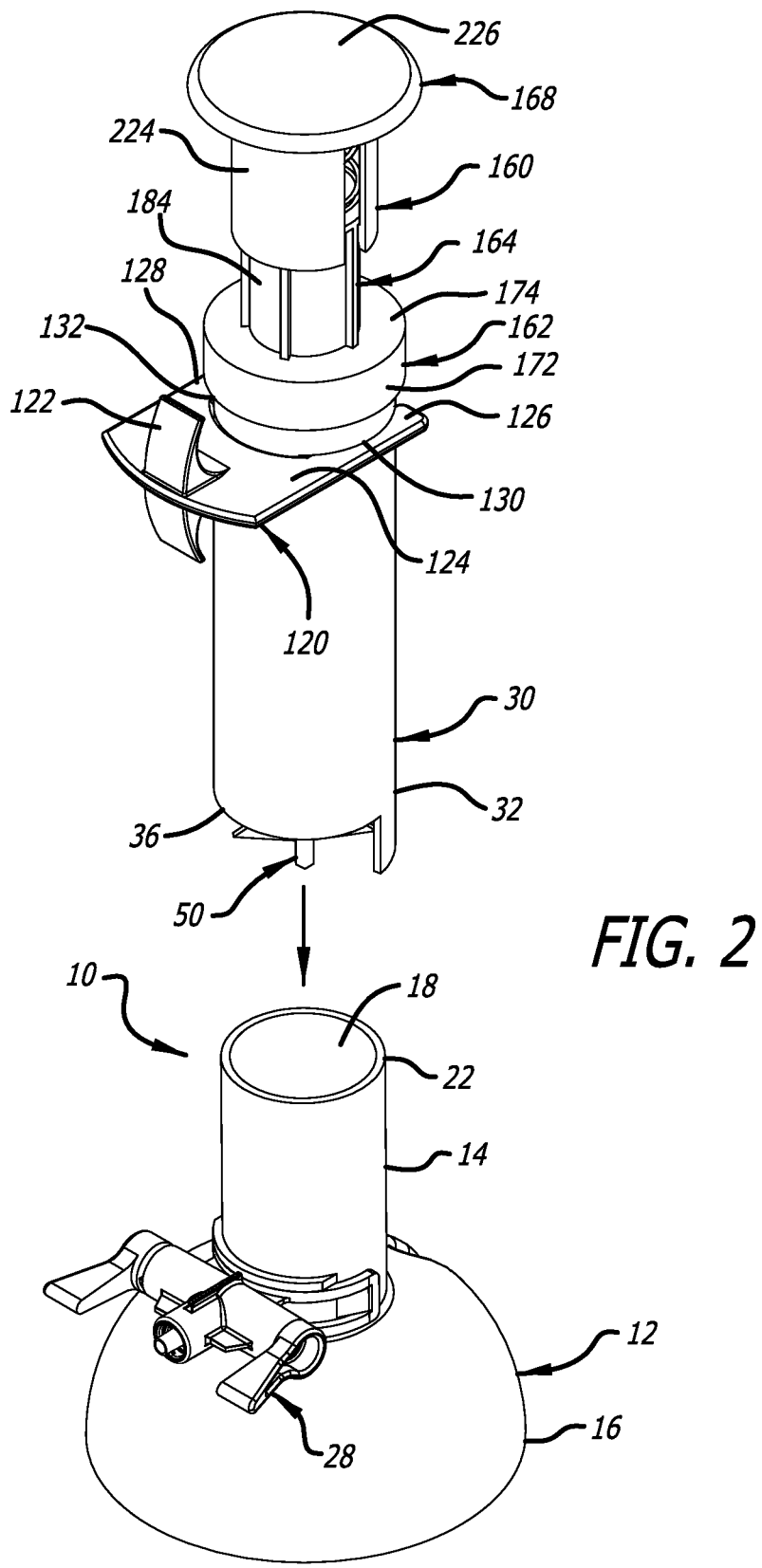
FIG. 2 is a partially-exploded perspective view of the manual mixer of FIG. 1.
Figure 4:
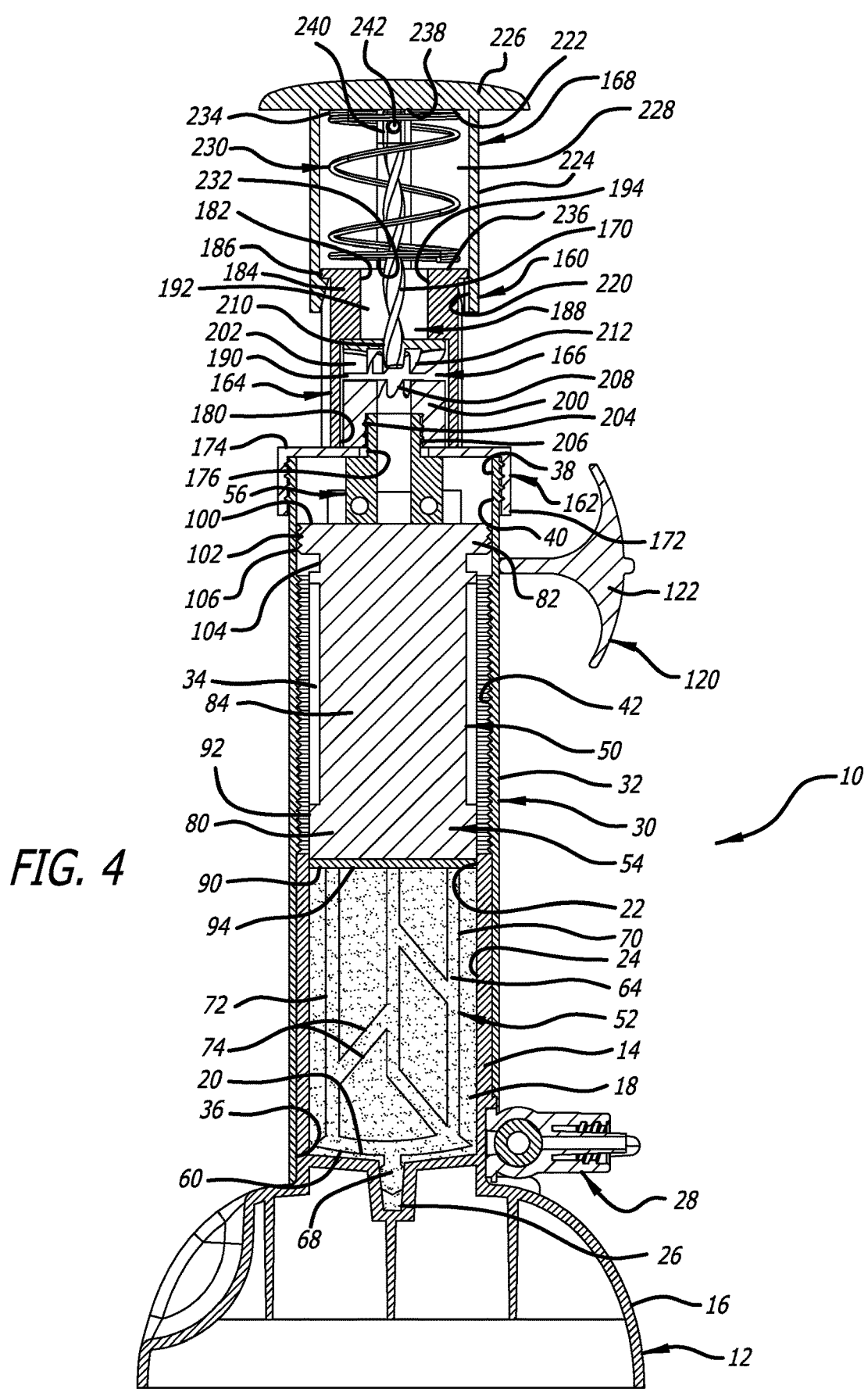
FIG. 4 is a cross-sectional view of the manual mixer of FIG. 1 showing a plunger portion thereof in an upper first position.
Figure 5:
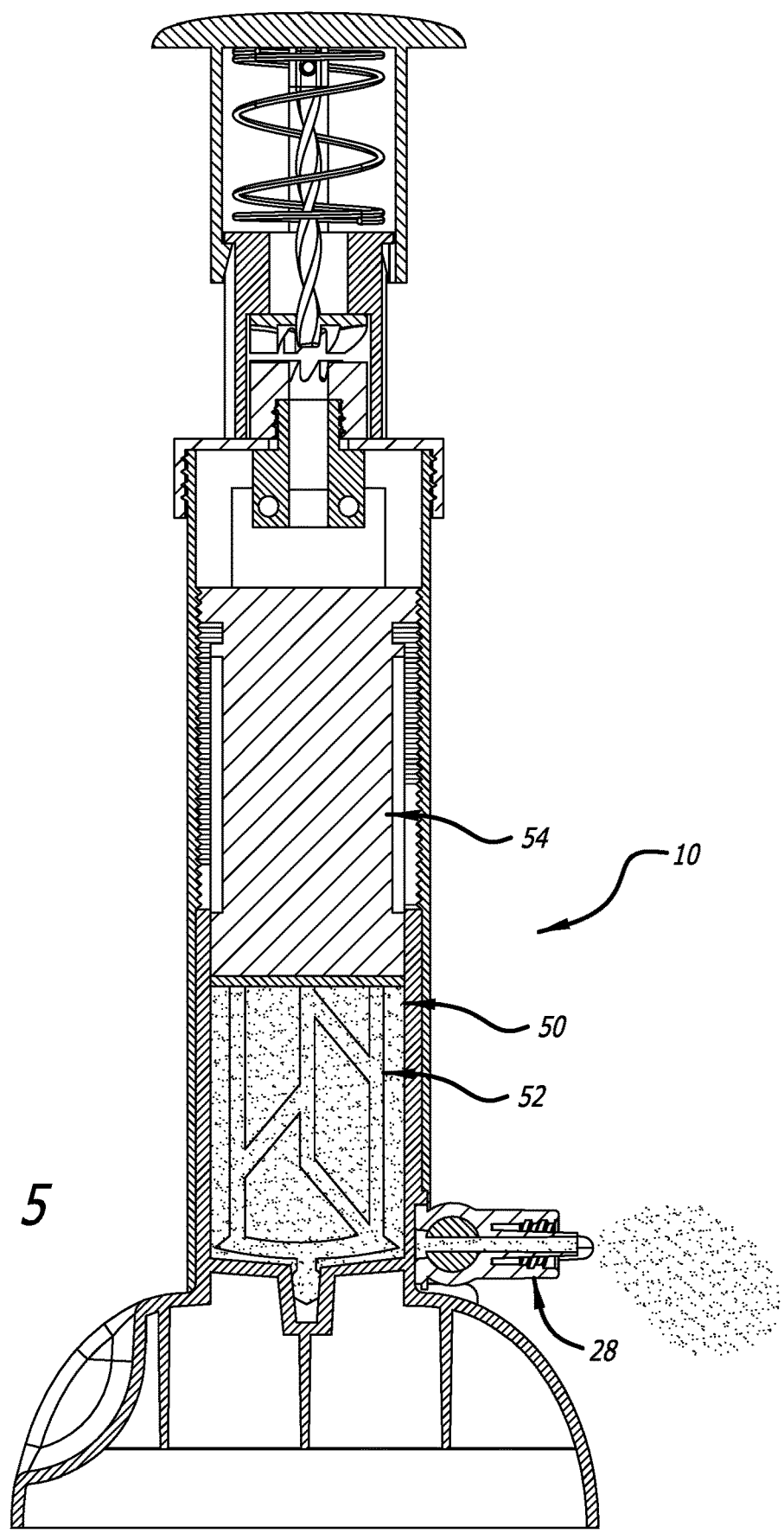
FIG. 5 is a cross-sectional view of the manual mixer similar to FIG. 4 showing the plunger portion in an intermediate position.
Figure 6:
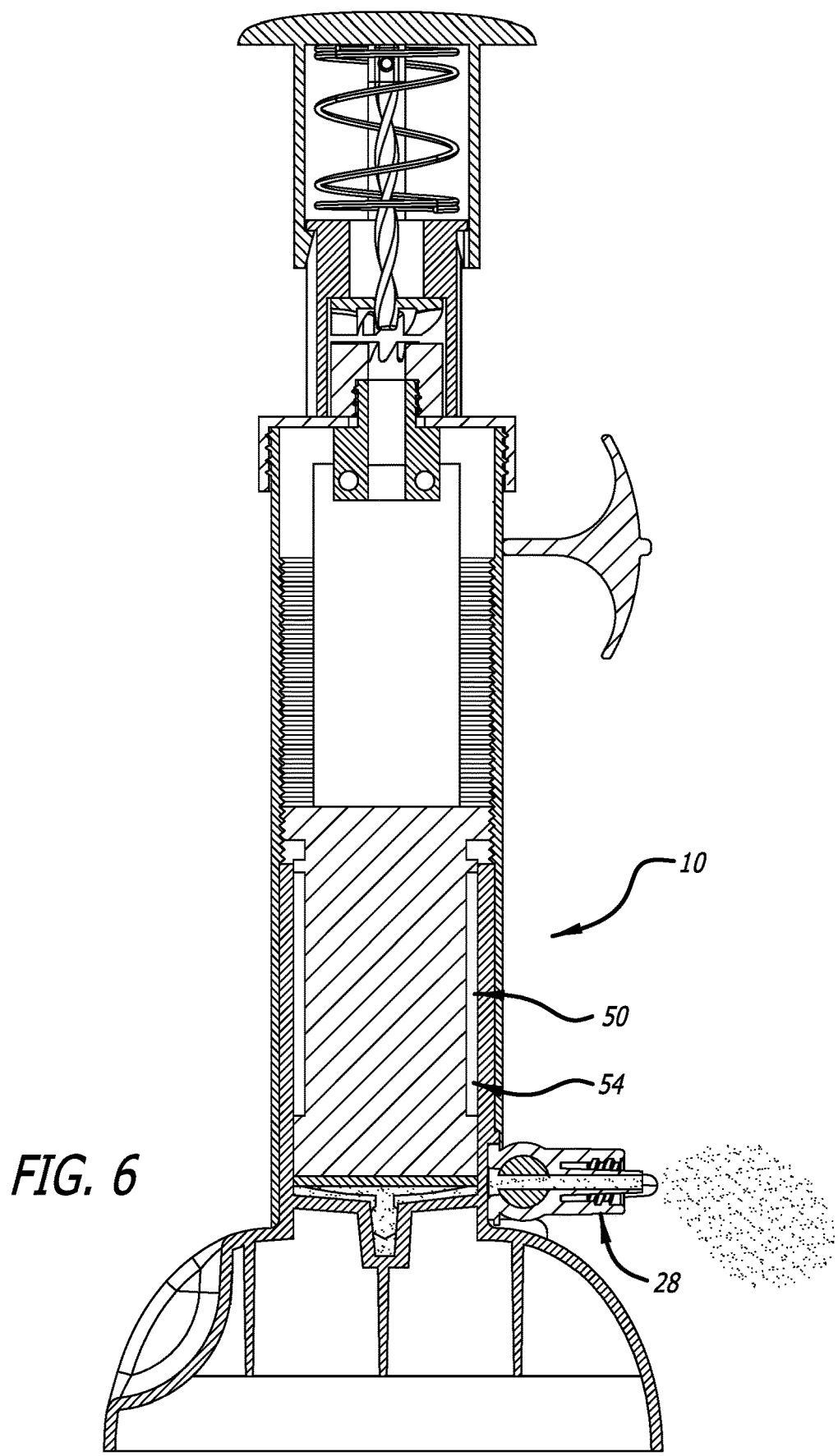
FIG. 6 is a cross-sectional view of the manual mixer similar to FIGS. 4 and 5 showing the plunger portion in a lower second position.

As depicted in FIGS. 1, 2, and 4, the manual mixer 10 includes a base portion 12, and the base portion 12 includes a first sidewall portion 14 and a pedestal portion 16. The first sidewall portion 14 extends upwardly from the pedestal portion 16, and the pedestal portion 16 serves as a stand allowing the base portion 12 to remain upright. The first sidewall portion 14 is hollow and in part defines a first interior cavity 18 having a closed first end 20, an open second end 22, and an interior surface 24. The interior surface 24 can be cylindrical. Furthermore, the pedestal portion 16 includes a depression 26 formed therein, and the depression 26 communicates with the first interior cavity 18.

As discussed below, the first interior cavity 18 along with other portions of the manual mixer 10 is provided to receive materials (including liquids, pastes, and/or solids) that can be mixed and agitated by the manual mixer 10 prior to use during surgery or other medical procedures. As such, the first interior cavity 18 serves as a mixing chamber. An example of a material that can be mixed using the manual mixer 10 is a bone cement such as polymethyl methacrylate (PMMA). The base portion 12 includes a valve assembly 28, and as discussed below, the valve assembly 28 can be closed to facilitate mixing and agitating the materials in the mixing chamber, and can be opened to facilitate dispensing of the materials from the mixing chamber.

The manual mixer 10, as depicted in FIGS. 1, 2, and 4, also includes a body portion 30, and the body portion 30 includes a second sidewall portion 32. The second sidewall portion 32 extends upwardly from adjacent the pedestal portion 16. The second sidewall portion 32 is hollow and in part defines a second interior cavity 34 having an open first end 36, an open second end 38, and an interior surface 40. Like the interior surface 24, the interior surface 40 can be cylindrical. The second sidewall portion 32 includes threads 42 formed along a portion of the interior surface 40.

The base portion 12 and the body portion 30 are removably attached to one another. To facilitate such removable attachment, a portion of the first sidewall portion 14 is received within the second interior cavity 34. As depicted in FIG. 4, when the base portion 12 and the body portion 30 are attached, portions of the first sidewall portion 14 and the second sidewall portion 32 overlap one another, a seal is created between the base portion 12 and the body portion 30, and the first interior cavity 18 and the second interior cavity 34 communicate with one another through the open second end 38. Furthermore, when the base portion 12 and the body portion 30 are detached, access is provided to the first interior cavity 18, and the first interior cavity 18 can receive the materials that are to be mixed and agitated by the manual mixer 10.

Figure 3:
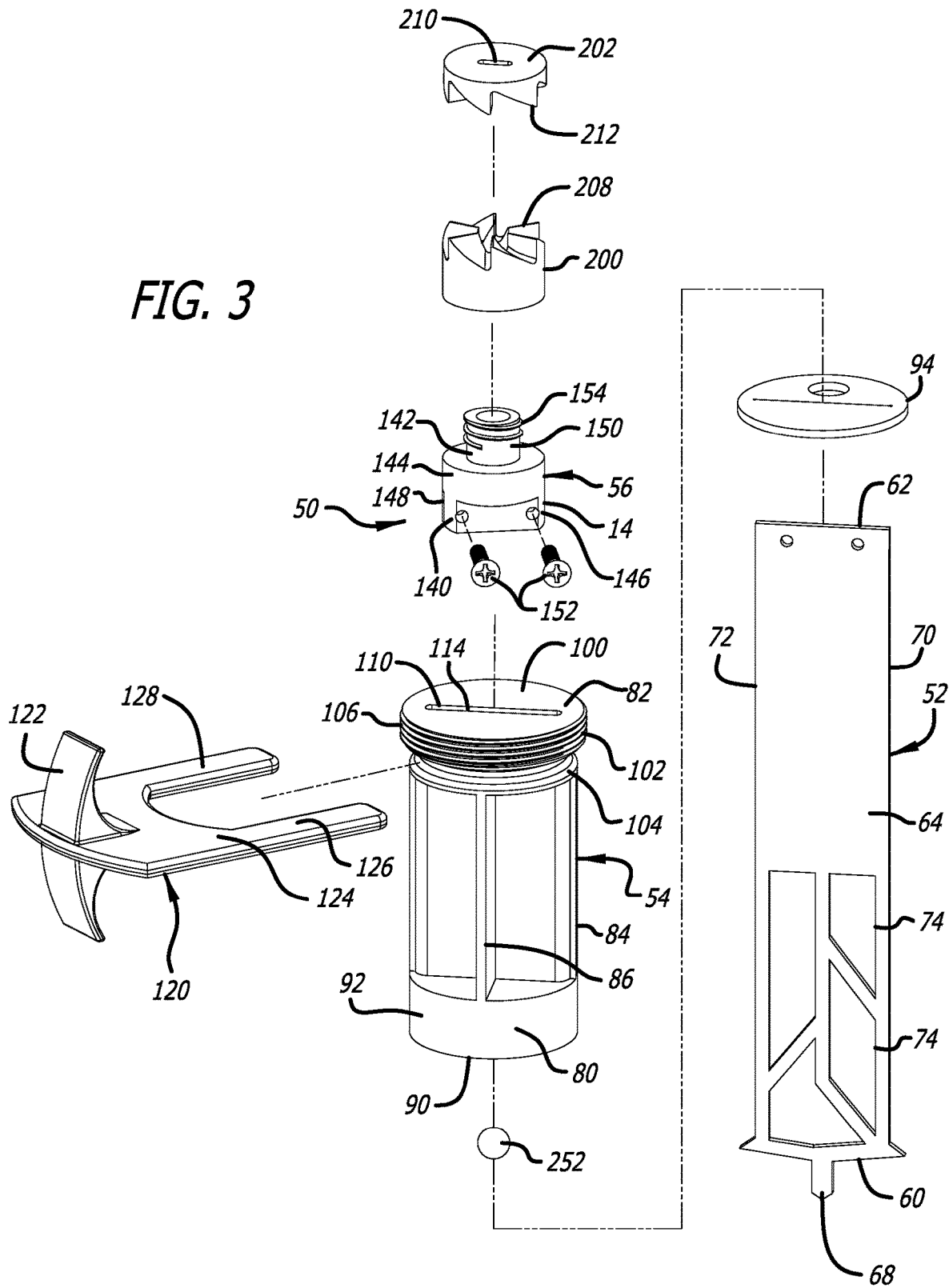
FIG. 3 is an exploded perspective view of a mixing assembly of the manual mixer of FIG. 1.

The manual mixer 10, as depicted in FIGS. 3 and 4, also includes a mixing assembly 50 provided in portions of the first interior cavity 18 and the second interior cavity 34 for mixing and agitating the materials provided therein. The mixing assembly 50 includes a paddle portion 52, a plunger portion 54, and a coupler portion 56.

The paddle portion 52 is capable of rotating within portions of the first interior cavity 18 and the second interior cavity 34. The paddle portion 52 includes a lower first end 60, an opposite upper second end 62, a length between the lower first end 60 and the upper second end 62, and an axis of rotation A extending along the length and through the lower first end 60 and the upper second end 62. The paddle portion 52 also includes a first surface 64, an opposite second surface (not shown), a first edge 70, and an opposite second edge 72. The first surface 64 and the second surface can each be planar or curved, the horizontal widths of the paddle portion 52 between the first edge 70 and the second edge 72 can be constant or variable, the horizontal widths are also less than the minimum side-to-side dimensions of the first interior cavity 18 and the second interior cavity 34, and the paddle portion 52 can include one or more openings 74 extending between the first surface 64 and the second surface. The first surface 64 and the second surface can be substantially planar, the horizontal widths between the first edge 70 and the second edge 72 can be substantially constant, and the paddle portion 52 can include four (4) openings 74 of various shapes and sizes. The asymmetrical arrangement and shapes of the openings 74 are provided to inhibit the plunger portion 54 from getting caught on the paddle portion 52. The asymmetrical arrangement and shapes of the openings are provided to facilitate improved mixing and agitating of the materials. In an alternative embodiment, the shape of the openings 74 and arrangement thereof can be identical and/or symmetrical.

The lower first end 60 of the paddle portion 52 includes a projection 68. As depicted in FIG. 4, the projection 68 can be received in the depression 26, and the projection 68 serves as the point of support for the rotation of the paddle portion 52 about the axis of rotation A. The rotation of the paddle portion 52 and the interaction of the materials in the first interior cavity 18 mixes and agitates the materials due to contact thereof with the first surface 64 and the second surface, the passage thereof around the first edge 70 and the second edge 72, and the passage thereof through the openings 74.

The plunger portion 54 is moveable along and rotates with the paddle portion 52. The plunger portion 54 is moveable along the paddle portion 52 between an upper first position (FIG. 4) and a lower second position (FIG. 6) and proceeds through various intermediate positions (e.g., FIG. 5) relative to the first interior cavity 18 and the second interior cavity 34. As depicted in FIGS. 3 and 4, the plunger portion 54 includes a first end portion 80, an opposite second end portion 82, a web portion 84 extending between the first end portion 80 and the second end portion 82, and first and second support struts 86 and 88 (not shown) on either side of the web portion 84. The first end portion 80 includes a first end surface 90 and an outer surface 92, and the second end portion 82 includes a second end surface 100, an outer surface 102, and a depression 104 adjacent the outer surface 102.

The first end surface 90 is circular and the outer surface 92 is cylindrical. The first end surface 90 can be provided on a seal 94 attached to the first end portion 80. The first end surface 90 contacts the materials received in the first interior cavity 18 as the plunger portion 54 moves from the upper first position to the lower second position, and the seal 94 and the outer surface 92 form a seal with the interior surface 24 to prevent the materials from leaking past the first end portion 80. Furthermore, the outer surface 102 is cylindrical and includes threads 106 therearound. As discussed below, the threads 106 are provided for engagement to the threads 42 formed on the interior surface 40 of the second sidewall portion 32.

A passageway 110 extends through the plunger portion 54 between a first opening 112 in the first end surface 90 and a second opening 114 in the second end surface 100. In doing so, the passageway 110 traverses through the first end portion 80 (and the seal 94), and then the web portion 84, and then the second end portion 82. At least a portion of the paddle portion 52 is received in the passageway 110 to attach the paddle portion 52 and the plunger portion 54 to one another, and, as discussed above, the plunger portion 54 is moveable along the paddle portion 52 between the upper first position and the lower second position. The seal 94 serves in preventing the material from the first interior cavity 18 from entering the passageway 110 through the first opening 112 as the plunger portion 54 moves along the paddle portion 52. Furthermore, the plunger portion 54 is capable of rotating with the paddle portion 52 as it moves between the upper first position and the lower second position.

The plunger portion 54 is maintained in the first upper position by a clamp portion 120, and in the first upper position, the threads 42 and the threads 106 are disengaged from one another. As depicted in FIGS. 1-3, the clamp portion 120 includes a handle portion 122 and a U-shaped portion 124 having a first arm 126 and a second arm 128. The second sidewall portion 32 includes a first slot 130 and a second slot 132 on opposite sides thereof. The first slot 130 and the second slot 132 communicate with the second interior cavity 34, and afford partial insertion of the first arm 126 and the second arm 128 into the second interior cavity 34 to engage the depression 104 formed on the plunger portion 54. For example, when the clamp portion 120 is engaged to the depression 104, the first arm 126 is received through the first slot 130 to engage the depression 104, and the second arm 128 is received through the second slot 132 to engage the depression 104. The plunger portion 54 is capable of rotation with the clamp portion 120 engaged thereto. Thus, the clamp portion 120 holds the plunger portion 54 in the upper first position, while simultaneously allowing the plunger portion 54 to rotate with the rotation of the paddle portion 52. When the clamp portion 120 is disengaged from the depression 104 and removed from the remainder of the manual mixer 10, the plunger portion 54 drops downwardly from the first upper position to engage the threads 42 and the threads 106 with one another. Due to the interaction of the threads 42 and the threads 106, rotation of the plunger portion 54 with rotation of the paddle portion 52 causes the plunger portion 54 to translate downwardly toward the second lower portion.

The coupler portion 56 includes a first portion 140 and a second portion 142. As depicted in FIGS. 3 and 4, the first portion 140 includes a flange portion 144, a first extension portion 146 extending downwardly from the flange portion 144, and a slot 148 provided through the first extension portion 146, and the second portion 142 includes a second extension portion 150 extending upwardly from the flange portion 144. A portion of the paddle portion 52 is received in the slot 148, and fasteners 152 can be received through the first extension portion 146 and the paddle portion 52 to attach the paddle portion 52 to the coupler portion 56. Furthermore, the second extension portion 150 is cylindrical and includes threads 154 for engagement to an actuation assembly 160 used to rotate the paddle portion 52 and the plunger portion 54. As such, the second extension portion 150 and the threads 154 serve as a coupler facilitating engagement of the coupler portion 56 to the actuation assembly 160.

The actuation assembly 160 includes a cap portion 162, a transmission housing 164, a transmission 166, a button portion 168, and a drive shaft 170. The cap portion 162, as depicted in FIG. 4, includes a sidewall portion 172, a top portion 174 extending between the sidewall portion 172, and an aperture 176 formed through the top portion 174. The cap portion 162 is received over the second sidewall portion 32 to enclose the second interior cavity 34, and the second extension portion 150 of the coupler portion 56 is received through the aperture 176.

The transmission housing 164, as depicted in FIG. 4, includes an open first end 180, an open second end 182, a sidewall portion 184 extending from the open first end 180 toward the open second end 182, a flange portion 186 at the open second end 182, and an interior cavity 188 extending between the open first end 180 and the open second end 182. The sidewall portion 184 at the open first end 180 can be attached to the top portion 174 of the cap portion 162. The interior cavity 188 includes a lower first portion 190 and an upper second portion 192. The lower first portion 190 receives a portion of the second extension portion 150, the transmission 166, and a portion of the drive shaft 170 therein. The upper second portion 192 receives a portion of the drive shaft 170 therein. Furthermore, the flange portion 186 is used to facilitate attachment of the button portion 168 to the transmission housing 164.

The transmission 166, as depicted in FIG. 4, includes a first gear 200 attached to the second extension portion 150, and a second gear 202 attached to the drive shaft 170. The first gear 200 includes an aperture 204, threads 206 provided in the aperture 204, and a first set of teeth 208, and the second gear 202 includes an aperture 210 and a second set of teeth 212. The threads 154 can engage the threads 206 to attach the second extension portion 150 to the first gear 200, and the drive shaft 170 can be received in the aperture 210 to attach the drive shaft 170 to the second gear 202. The first set of teeth 208 and the second set of teeth 212 can matingly engage one another, and when engaged, rotation of the second gear 202 causes corresponding rotation of the first gear 200.

The button portion 168, as depicted in FIG. 4, includes an open first end 220, a closed second end 222, a sidewall portion 224 extending from the open first end 220 toward the closed second end 222, a handhold portion 226 at the closed second end 222, and an interior cavity 228 extending from the open first end 220 toward the closed second end 222. The button portion 168 is moveable between an upper first position and a lower second position relative to the transmission housing 164, and depending on the position of the button portion 168 more or less of the transmission housing 164 is received in the interior cavity 228.

A spring 230 having a first end 232 and a second end 234 is provided in the interior cavity 228. The first end 232 engages a top surface 236 of the flange portion 186, and the second end 234 engages an upper interior surface 238 of the interior cavity 228 adjacent the handhold portion 226. The spring 230 biases the button portion 168 in the upper first position. Furthermore, the upper interior surface 238 includes a projection portion 240 extending into the interior cavity 228. The drive shaft 170 is attached to the projection portion 240 using a fastener 242. As such, the drive shaft 170 moves with the button portion 168. When the handhold portion 226 is moved downwardly, the drive shaft 170 also moves downwardly, and when the handhold portion 226 is moved upwardly, the drive shaft 170 also moves upwardly.

As discussed below, downward strokes of the button portion 168 causes downward movement of the drive shaft 170, and the interaction of the drive shaft 170 with the transmission 166 due to the movement thereof ultimately causes rotation of the paddle portion 52 and the plunger portion 54.

As discussed above, the drive shaft 170 is received through the aperture 210 of the second gear 202. The interaction between the drive shaft 170 and the aperture 210 at times causes the second gear 202 to move with drive shaft 170 and at other times causes the drive shaft 170 to slide through the aperture 210. Friction between the drive shaft 170 and the walls of the aperture 210 causes the second gear 202 to move with the drive shaft 170, and overcoming the friction between the drive shaft 170 and the walls of the aperture 210 causes the drive shaft 170 to slide through the aperture 210.

When the button portion 168 is in the upper first position, the drive shaft 170 is located at an uppermost position and the second gear 202 is disengaged from the first gear 200. When the button portion 168 is depressed downward toward the lower second position, the drive shaft 170 is moved downwardly and friction causes the second gear 202 to move downwardly with the drive shaft 170. Such downward movement causes the second gear 202 to engage the first gear 200. In doing so, the first set of teeth 208 and the second set of teeth 212 are matingly engaged with one another. After engagement of the second gear 202 with the first gear 200, further downward movement of the button portion 168 causes the drive shaft 170 to slide through the aperture 210. Due to the helical shape of the drive shaft 170, sliding movement of the drive shaft 170 through the aperture 210 causes the second gear 202 to rotate in a first direction. Thus, pushing the button portion 168 downwardly causes rotation of the second gear 202 and corresponding rotation of the first gear 200 in the first direction. Because first gear 200 is attached to the coupler portion 56, and the coupler portion 56 is attached to the paddle portion 52, such rotation causes rotation of the paddle portion 52 and the plunger portion 54 in the first direction.

When the button portion 168 is released, the spring 230 causes the button portion 168 to return to the upper first position. Releasing the button portion 168 also disengages the second gear 202 from the first gear 200 to prevent further rotation of the first gear 200 in the first direction or in an opposite second direction. As such, rotation of the first gear 200 (and ultimately rotation of the paddle portion 52 and the plunger portion 54) only occurs during downward strokes of the button portion 168.

Figure 7:
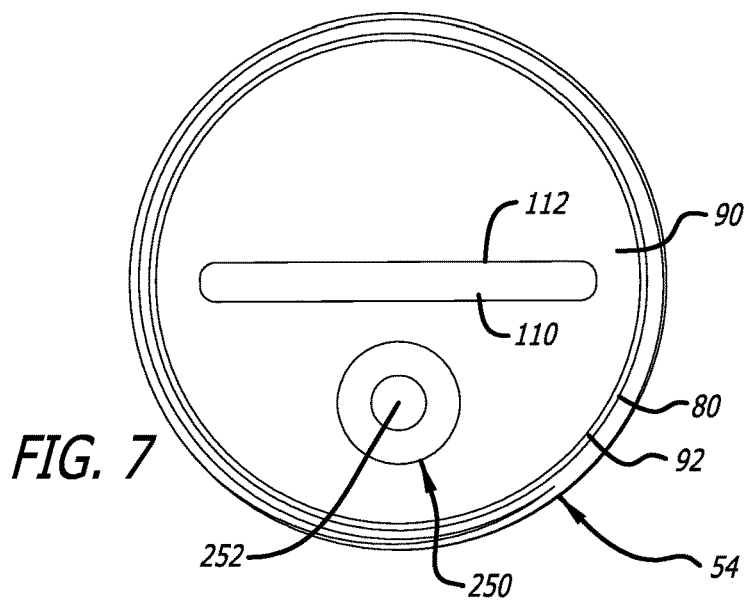
FIG. 7 is a bottom plan view of the plunger portion of the manual mixer of FIG. 1 showing a check valve.
Figure 8:
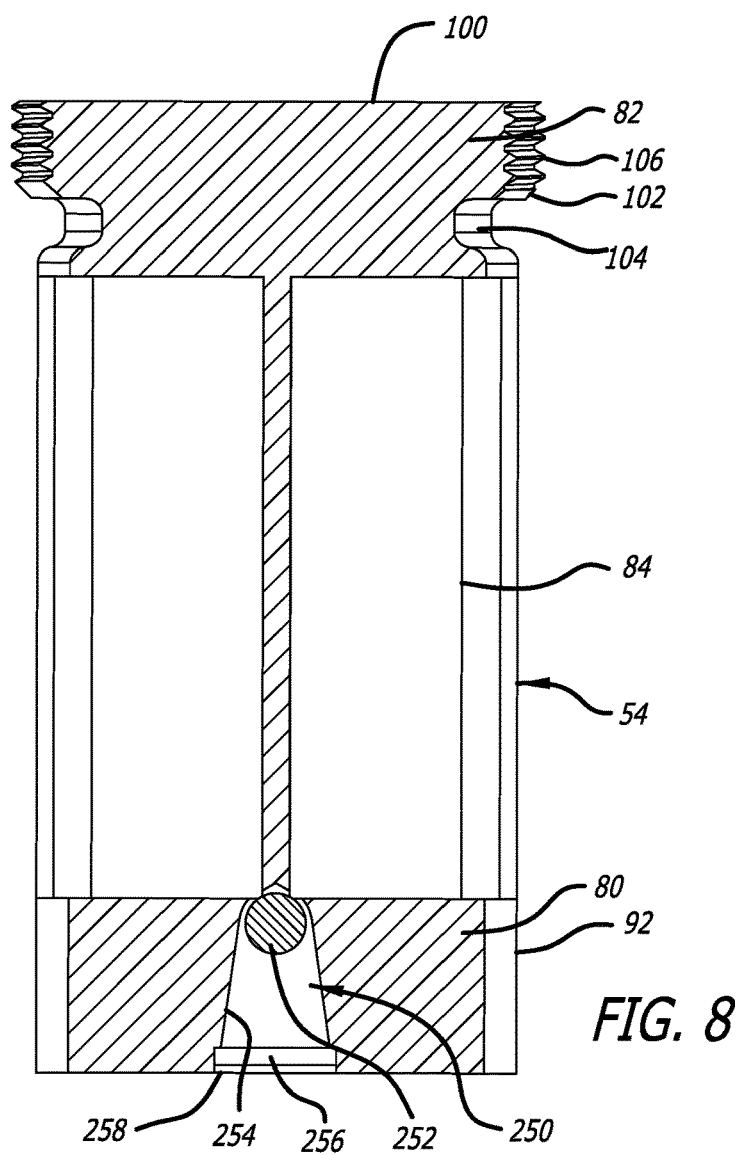
FIG. 8 is a cross-sectional view of the plunger portion of the manual mixer of FIG. 1 showing the check valve.

As depicted in FIGS. 7 and 8, the plunger portion 54 can include a ball check valve 250 to facilitate release of air contained in the first interior cavity 18. The ball check valve 250 includes a ball 252, a cavity 254 for receiving the ball 252, and a washer 256 for containing the ball 252 in the cavity 254. The cavity 254 is formed in a portion of the first end portion 80 and can be conical. The cavity 254 communicates with both the first interior cavity 18 via an aperture 258 in the first end surface 90 and atmosphere via passages provided at or adjacent the apex of the cavity 254. The washer 256 holds the ball 252 in the cavity 254, while still allowing air and the material from the first interior cavity 18 to enter the cavity 254. As the plunger portion 54 translates downwardly, air from the first interior cavity 18 enters the cavity 254. Air entering the cavity 254 does not have enough pressure to push the ball 252 upwardly to cover the passages provided at the apex of the cavity 254. Thus, air entering the cavity 254 from the first interior cavity 18 can be vented to atmosphere. However, when the materials from the first interior cavity 18 enter the cavity 254, the materials do have enough pressure to push the ball 252 upwardly to cover the passages provided at the apex of the cavity 254. As such, the ball check valve 250 allows air from the first interior cavity 18 to vent to atmosphere, but also prevents the materials from the first interior cavity 18 from escaping therefrom.

During use of the manual mixer 10, the base portion 12 and the body portion 30 are initially detached from one another to afford access to the first interior cavity 18. As discussed above, the first interior cavity 18 serves as a mixing chamber. As such, the first interior cavity 18 can be filled with the materials requiring mixing and agitated by the manual mixer 10. Once filled with a selected amount of the materials, the base portion 12 and the body portion 30 can be attached to one another. As discussed above, a seal is created between the base portion 12 and the body portion 30 when attached to one another. The seal serves in preventing the materials from escaping the interior cavity.

To initially mix and agitate the materials in the first interior cavity 18, the clamp portion 120 is engaged to the manual mixer 10, and the valve assembly 28 is closed to facilitate containment of the materials in the first interior cavity 18 during such mixing and agitating. As discussed above, the clamp portion 120 holds the plunger portion 54 in the upper first position, while simultaneously allowing the plunger portion 54 to rotate with the rotation of the paddle portion 52. Actuation of the actuation assembly 160 rotates the paddle portion 52 and the plunger portion 54, and rotation of the paddle portion 52 in the first interior cavity 18 serves to mix and agitate the materials received therein. The valve assembly 28 is closed to facilitate containment of the materials in the first interior cavity 18 during such mixing and agitating.

When mixing and agitating is determined to be complete, the clamp portion 120 is disengaged from the manual mixer 10, and the valve assembly 28 is opened to facilitate dispending of the materials from the first interior cavity 18. After disengagement of the clamp portion 120, the plunger portion 54 drops downwardly from the first upper portion to engage the threads 42 and the threads 106 with one another. As discussed above, due to the interaction of the threads 42 and the threads 106, rotation of the paddle portion 52 and plunger portion 54 causes the plunger portion 54 to move downwardly toward the second lower portion. The downward translation of the plunger portion 54 forces the materials in the first interior cavity 18 to be dispensed through the valve assembly 28. When the plunger portion 54 completes its translation to the lower second position, the material in the first interior cavity 18 will have been fully dispensed therefrom with minimal waste material remaining in the first interior cavity 18.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A manual mixer for mixing and agitating materials for use during surgery, the manual mixer comprising:
 a base portion having a first sidewall portion and a pedestal portion, the first sidewall portion extending upwardly from the pedestal portion and defining at least in part a first interior cavity;
 a body portion having a second sidewall portion, the second sidewall portion extending upwardly from adjacent the pedestal portion and defining at least in part a second interior cavity, an interior surface of the second sidewall including first threads, and a portion of first sidewall being received with the second interior cavity;
 a mixing assembly having a paddle portion and a plunger portion, the paddle portion and the plunger portion being provided in portions of the first interior cavity and the second interior cavity, the paddle portion including an upper first end, a lower second end, a first side extending between the upper first end and the lower second end, and a second side extending between the upper first end and the lower second end, the plunger portion including an upper first end, a lower second end, a passageway extending through the plunger portion between the upper first end and the lower second end thereof, and second threads between the upper first end and the lower second end of the plunger portion for engaging the first threads formed on the interior surface of the second sidewall, at least a portion of the paddle portion being moveably received in the passageway, the plunger portion being moveable along the paddle portion between an upper first position and a lower second position; and
 an actuation assembly attached to the body portion, and having a transmission housing, a transmission, and a drive shaft, the transmission housing defining a third interior cavity, the transmission and a portion of the drive shaft being received in the third interior cavity, the transmission being operatively engaged to the paddle portion and the drive shaft via a first gear of the transmission connected to the paddle portion and a second gear of the transmission connected to the drive shaft, the second gear being moveable between an upper third position where the first gear and the second gear are disengaged from one another, and a lower fourth position where the first gear and the second gear are engaged to one another;
 wherein actuation of the actuation assembly causes linear movement of the drive shaft to move the second gear from the upper third position to the lower fourth position to engage the second gear to the first gear, and the linear movement of the drive shaft is translated into rotational movement by the transmission causing corresponding rotation of the paddle portion and the plunger portion moveably attached to the paddle portion via engagement of the first gear and the second gear.

2. The manual mixer of claim 1, wherein, when the second gear is contacted with the first gear, and when the first threads and the second threads are engaged, further linear movement of the drive shaft via actuation of the actuation assembly causes further rotational movement of the paddle portion and the plunger portion that translates into linear movement of the plunger portion due to interaction of the first threads and the second threads.

3. The manual mixer of claim 2, further comprising a clamp portion receivable in the second interior cavity for engaging the plunger portion to maintain the plunger portion in position in the upper first position.

4. The manual mixer of claim 3, wherein, when the clamp portion is received in the second interior cavity and engaged to the plunger portion, the first threads and the second threads are disengaged from one another, and the plunger portion remains in the upper first position during rotation thereof, and, when the clamp portion is removed from the second interior cavity and disengaged from the plunger portion, the plunger portion moves downwardly to engage the first threads and the second threads, and the plunger portion translates toward the lower second position during rotation thereof due to the interaction of the first threads and the second threads.

5. The manual mixer of claim 1, wherein the actuation assembly further comprises a button portion, the button portion being operatively interconnected via the drive shaft to the transmission, and wherein linear movement of the button from an upper fifth position to a lower sixth position causes linear movement of the drive shaft to actuate the actuation assembly.

6. The manual mixer of claim 5, wherein, when the second gear is contacted with the first gear, and when the first threads and the second threads are engaged, further linear movement of the drive shaft via linear movement of the button portion causes further rotational movement of the paddle portion and the plunger portion that translates into linear movement of the plunger portion toward the base portion due to interaction of the first threads and the second threads.

7. The manual mixer of claim 6, wherein the drive shaft includes a helical portion, and the second gear includes a wall portion and an aperture provided in the wall portion, the aperture being configured to receive the drive shaft therein, interaction between the drive shaft and the aperture due to movement of the drive shaft therethrough causes rotation of the second gear.

8. The manual mixer of claim 1, wherein the paddle portion includes a projection at the lower second end thereof, and the pedestal portion includes a depression for receiving the projection therein, the interaction of the projection in the depression facilitating the rotation of the paddle portion.

9. A manual mixer for mixing and agitating materials for use during surgery, the manual mixer comprising:
   a base portion having a first sidewall portion, the first sidewall portion defining at least in part a first interior cavity;
   a body portion having a second sidewall portion, the second sidewall portion defining a second interior cavity, a first portion of the second sidewall portion being overlapped with at least a portion of the first sidewall portion, and a second portion of the second sidewall portion including an interior surface including first threads;
   a mixing assembly having a paddle portion and a plunger portion, the paddle portion and the plunger portion being provided in portions of the first interior cavity and the second interior cavity, the paddle portion including an upper first end, a lower second end, an at least partially-planar first side extending between the upper first end and the lower second end, and an at least partially-planar second side extending between the upper first end and the lower second end, the plunger portion including an upper first end, a lower second end, a passageway extending through the plunger portion between the upper first end and the lower second end thereof, and second threads between the upper first end and the lower second end of the plunger portion for engaging the first threads formed on the interior surface of the second sidewall, at least a portion of the paddle portion being moveably received in the passageway;
   an actuation assembly attached to the body portion, and having a transmission housing, a transmission, and a drive shaft, the transmission housing defining a third interior cavity, the transmission and a portion of the drive shaft being received in the third interior cavity, the transmission being operatively engaged to the paddle portion and the drive shaft via a first gear of the transmission connected to the paddle portion and a second gear of the transmission connected to the drive shaft, the second gear being moveable between an upper first position where the first gear and the second gear are disengaged from one another, and a lower second position where the first gear and the second gear are engaged to one another;
   wherein actuation of the actuation assembly causes linear movement of the drive shaft to move the second gear from the upper first position to the lower second position to engage the second gear to the first gear, and the linear movement of the drive shaft is translated into rotational movement by the transmission causing corresponding rotation of the paddle portion and the plunger portion moveably attached to the paddle portion via engagement of the first gear and the second gear.

10. The manual mixer of claim 9, wherein, when the second gear is contacted with the first gear, and when the first threads and the second threads are engaged, further linear movement of the drive shaft via actuation of the actuation assembly causes further rotational movement of the paddle portion and the plunger portion that translates into linear movement of the plunger portion due to interaction of the first threads and the second threads.

11. The manual mixer of claim 9, further comprising a clamp portion receivable in the second interior cavity for engaging the plunger portion to maintain the plunger portion in position to prevent engagement of the first threads and the second threads.

12. The manual mixer of claim 11, wherein, when the clamp portion is received in the second interior cavity and engaged to the plunger portion, the first threads and the second threads are disengaged from one another, and, when the clamp portion is removed from the second interior cavity and disengaged from the plunger portion, the plunger portion moves downwardly to engage the first threads and the second threads, and the plunger portion translates toward the base portion during rotation thereof due to the interaction of the first threads and the second threads.

13. The manual mixer of claim 9, wherein the actuation assembly further comprises a button portion, the button portion being operatively interconnected via the drive shaft to the transmission, and wherein linear movement of the button from an upper third position to a lower fourth position causes linear movement of the drive shaft to actuate the actuation assembly.

14. The manual mixer of claim 13, wherein, when the second gear is contacted with the first gear, and when the first threads and the second threads are engaged, further linear movement of the drive shaft via linear movement of the button portion causes further rotational movement of the paddle portion and the plunger portion that translates into linear movement of the plunger portion toward the base portion due to interaction of the first threads and the second threads.

15. The manual mixer of claim 14, wherein the drive shaft includes a helical portion, and the second gear includes a wall portion and an aperture provided in the wall portion, the aperture being configured to receive the drive shaft therein, interaction between the drive shaft and the aperture due to movement of the drive shaft therethrough causes rotation of the second gear.

16. A manual mixer for mixing and agitating materials for use during surgery, the manual mixer comprising:
   a base portion defining at least in part a first interior cavity;
   a body portion having a sidewall portion, the sidewall portion defining a second interior cavity, a first portion of the sidewall portion being overlapped with at least a portion of the base portion, and a second portion of the sidewall portion including an interior surface including first threads;

a mixing assembly having a paddle portion and a plunger portion, the paddle portion and the plunger portion being provided in portions of the first interior cavity and the second interior cavity, the paddle portion including an upper first end, a lower second end, and at least partially planar portions provided between the upper first end and the lower second end, the plunger portion including an upper first end, a lower second end, a passageway extending through the plunger portion between the upper first end and the lower second end thereof, and second threads between the upper first end and the lower second end of the plunger portion for engaging the first threads formed on the interior surface of the sidewall, at least a portion of the paddle portion being moveably received in the passageway;

an actuation assembly attached to the body portion, and having a transmission housing, a transmission, and a drive shaft, the transmission housing defining a third interior cavity, the transmission and a portion of the drive shaft being received in the third interior cavity, the transmission being operatively engaged to the paddle portion and the drive shaft via a first gear of the transmission connected to the paddle portion and a second gear of the transmission connected to the drive shaft, the second gear being moveable between an upper first position where the first gear and the second gear are disengaged from one another, and a lower second position where the first gear and the second gear are engaged to one another;

wherein actuation of the actuation assembly causes linear movement of the drive shaft to move the second gear from the upper first position to the lower second position to engage the second gear to the first gear, and the linear movement of the drive shaft is translated into rotational movement by the transmission causing corresponding rotation of the paddle portion and the plunger portion moveably attached to the paddle portion via engagement of the first gear and the second gear, and interaction of the first threads and the second threads during the rotation of the paddle portion and the plunger portion moves the plunger portion toward the base portion.

17. The manual mixer of claim 16, further comprising a clamp portion receivable in the second interior cavity for engaging the plunger portion to maintain the plunger portion in position to prevent engagement of the first threads and the second threads.

18. The manual mixer of claim 17, wherein, when the clamp portion is received in the second interior cavity and engaged to the plunger portion, the first threads and the second threads are disengaged from one another, and, when the clamp portion is removed from the second interior cavity and disengaged from the plunger portion, the plunger portion moves downwardly to engage the first threads and the second threads, and the plunger portion translates toward the base portion during rotation thereof due to the interaction of the first threads and the second threads.

19. The manual mixer of claim 16, wherein the actuation assembly further comprises a button portion, the button portion being operatively interconnected via the drive shaft to the transmission, and wherein linear movement of the button from an upper third position to a lower fourth position causes linear movement of the drive shaft to actuate the actuation assembly.

20. The manual mixer of claim 16, wherein the drive shaft includes a helical portion, and the second gear includes a wall portion and an aperture provided in the wall portion, the aperture being configured to receive the drive shaft therein, interaction between the drive shaft and the aperture due to movement of the drive shaft therethrough causes rotation of the second gear.

* * * * *